United States Patent [19]
Dunstan et al.

[11] Patent Number: 5,525,147
[45] Date of Patent: Jun. 11, 1996

[54] PREVENTATIVE TREATMENT OF WOOD

[75] Inventors: Richard C. Dunstan, Redmond; John F. Bartlett, Kent, both of Wash.

[73] Assignee: Perma-Chink Systems, Inc., Redmond, Wash.

[21] Appl. No.: 548,276

[22] Filed: Oct. 25, 1995

Related U.S. Application Data

[63] Continuation-in-part of Ser. No. 199,481, Feb. 22, 1994, abandoned.

[51] Int. Cl.$^6$ ................................................ A01N 59/14
[52] U.S. Cl. .................... 106/18.3; 424/657; 424/658; 424/659; 424/660; 252/380; 252/383
[58] Field of Search .......................... 106/18.3; 424/657, 424/658, 659, 660; 252/380, 383

[56] References Cited

U.S. PATENT DOCUMENTS

| | | | |
|---|---|---|---|
| 4,461,721 | 7/1984 | Goettsche et al. | 252/607 |
| 4,610,881 | 9/1986 | Bechgaard | 424/148 |
| 4,801,404 | 1/1989 | Dietrich et al. | 252/607 |
| 5,104,664 | 4/1992 | Palmere et al. | 424/660 |
| 5,129,946 | 7/1992 | Evans | 106/18.3 |
| 5,151,127 | 9/1992 | Thompson | 106/15.05 |

OTHER PUBLICATIONS

Treatment of Log–Home Logs with Thickened Boron, Puettman et al., 42 Forest Products Journal 11/12, Nov./Dec. 1992, pp. 30–32.

BORA–CARE Termiticide, Insecticide and Fungicide Concentrate.

U.S. Borax Service Bulletin 200 & Specimen Label, Sep. 1992.

*Primary Examiner*—Anthony Green
*Attorney, Agent, or Firm*—Hughes, Multer & Schacht

[57] ABSTRACT

Methods and compositions for protecting wooden members (components) against attack by destructive insects and fungi. The wood preservative is formulated as a paste and is applied in that form to an exposed surface of the member. The active ingredient is released by that same moisture which creates conditions conducive to destructive attacks on the wood. Boron-based active ingredients are preferred as are polyethylene glycol carriers for the active ingredient.

9 Claims, 2 Drawing Sheets

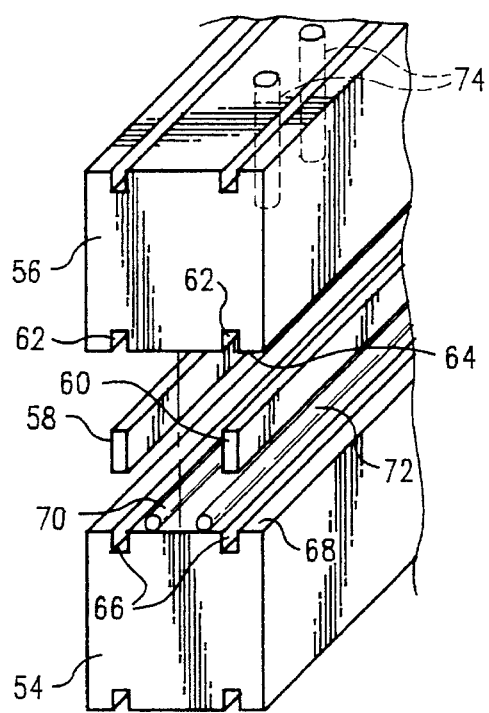
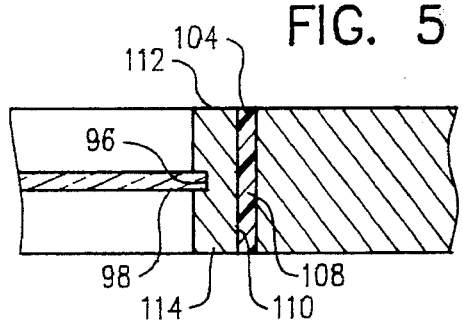
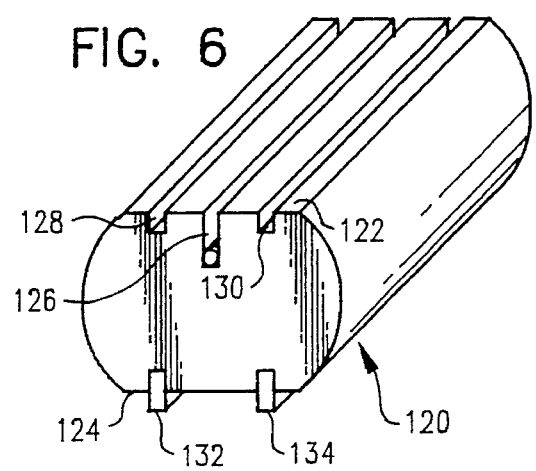
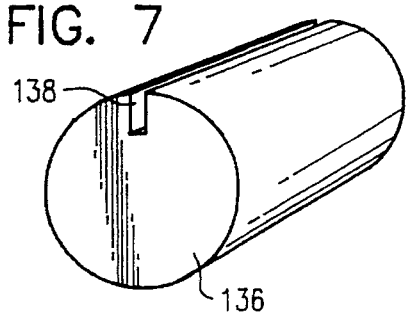
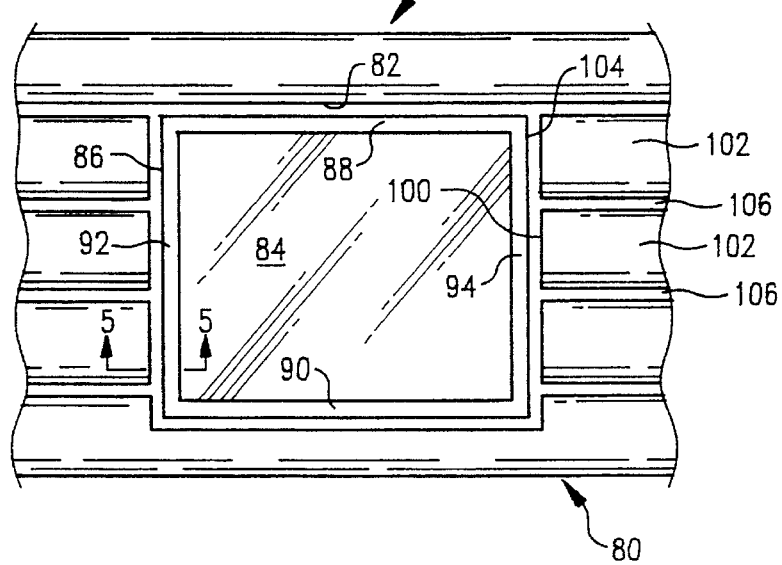

PREVENTATIVE TREATMENT OF WOOD

RELATED APPLICATION

This application is a continuation-in-part of application Ser. No. 08/199,481 filed 22 February 1994 now abandoned.

TECHNICAL FIELD OF THE INVENTION

The present invention relates to novel, improved methods and formulations for protecting wood against insecticidal and fungal attack.

BACKGROUND OF THE INVENTION

Logs, lumber, and other forms of wood are susceptible to attack by a variety of destructive insects, larvae, and fungi including: Subterranean, Dampwood, and Drywood termites; wood boring beetles; carpenter ants; and fungi such as *Poria sp., Polyporous sp., Coniophora cerebella, C. putriana, Lenzitis sapiara, L. tribium, Merulius lacrymans, Poxillus sp., Xestobium rufivollosum, Anobium punctatum, A. mollis,* and *Callidum viollacem.* Other partial lists of insects and fungi that cause wood damage can be found in BORA-CARE™, Termiticide Insecticide and Fungicide Concentrate and in U.S. Borax Service Bulletin & Specimen Label 200.

There are many treatment agents and application techniques designed to protect wood against attack by the foregoing and other insects and fungi. The compounds commonly used for such treatment agents comprise an active ingredient which actually kills the insects, fungi, etc., and a carrier which functions to carry the active ingredient into the wood by diffusion. A commonly used active ingredient is a boron composition such as disodium octoborate tetrahydrate (DOT), marketed under the trademark TIMBOR. Commonly, such a boron compound is provided: (1) in an aqueous carrier; (2) in a liquid carrier and penetration aid such as a mixture of ethylene glycol and water (U.S. Pat. No. 4,610,881 issued 9 September 1986 to Bechgaard) or a mixture of polyethylene and ethylene glycols (U.S. Pat. No. 5,104,664 issued 14 April 1992 to Palmere et al.); or (3) in a microcrystalline formulation which is subsequently diluted with water and used as a dip or spray (U.S. Pat. No. 5,129,946 issued 14 July 1992 to Evans and Treatment of Log-Home Logs with Thickened Boron, Puettmann et al., 42 Forest Products Journal 11/12, November/December 1992, pp 30–32).

The foregoing, and similar, products have significant drawbacks. Those which contain ethylene glycol are unsafe (ethylene glycol is classified as a toxic chemical). The active principles in boron-based products with an aqueous carrier do not diffuse well into dry wood. Water evaporates too quickly for it to transport the active ingredient to the center of a wooden component of significant thickness.

Available alternatives to the boron-based wood preservatives discussed above are fumigants, pesticides, and pressure treatment formulations which contain CCA (chromated copper arsenate) and other toxic compounds containing copper, chromium, or arsenic. Pressure treated logs are also unpopular as the preservative turns the wood green. Or, if a stain is added to the formulation, it gives what is regarded by some as an unnatural appearance which is incompatible with the desired look of log homes.

As will be apparent to the reader, there is a continuing and present need for an improved way of protecting woods against attack by destructive insects and fungi.

SUMMARY OF THE INVENTION

There have now been invented and disclosed herein certain new and novel preservatives and application techniques with the capability of realizing this important objective.

The novel wood preservatives of the present invention employ boron compounds as the active, pesticidally effective ingredient. These compounds are efficacious and, as discussed above, relatively harmless to animal life.

The boron compound is dispersed in a carrier system containing water-miscible, non-toxic glycols with low volatility. The resulting formulation is a paste (for the purpose of this disclosure, a paste is defined as a smooth, thick, non-flowable composition which has much the same consistency as toothpaste and is sufficiently viscous to retain its form at the temperatures at which it is formulated and at the ambient temperatures to which it is subjected during storage and application, yet soft enough to be extruded from an applicator and to be formed into contact with the surface of a wooden member to which the paste is applied). The paste is applied to the wood to be treated as a bead, much like caulking, or forced into holes present or drilled in the wood, for example.

Thus applied, the preservative remains in place on or within the wood structure until dispersed or diffused by moisture in the wood and/or the carrier component of the product. At that point, the active principle is released from the paste and transported into and throughout the wood by the moisture as assisted by the glycol penetration aids. This complete penetration optimizes the efficacy of the boron-based pesticide by making it present throughout the volume of the wooden beam or other component to which the paste is applied. Because it is released only when moisture is present, effective amounts of the active principle remain available for long periods of time.

Also, as suggested above, the novel formulations of the present invention are free of the toxic ethylene glycol heretofore commonly employed as a carrier for boron compounds in wood preservative formulations. Furthermore, those carrier constituents which are employed are not hazardous.

The objects, features, and advantages of the invention will be apparent to the reader from the foregoing and the appended claims and as the ensuing detailed description and discussion proceeds in conjunction with the accompanying drawing.

BRIEF DESCRIPTION OF THE DRAWING

FIG. 3 is a view, similar to FIG. 2, of a structure composed of splined timbers;

FIG. 4 is a fragmentary side view of a log structure showing how the preservative is employed to protect the wood at openings such as the illustrated window;

FIG. 5 is a section through FIG. 5, taken substantially along line 5—5 of the latter figure.

FIG. 6 is an isometric view showing a portion of another type of timber having two flattened surfaces with which the composition of the present invention can advantageously be used; and FIG. 7 is an isometric view similar to FIG. 6, showing a round timber having a radial kerf with which the present invention can advantageously be used.

DETAILED DESCRIPTION OF THE INVENTION

Figure 1:
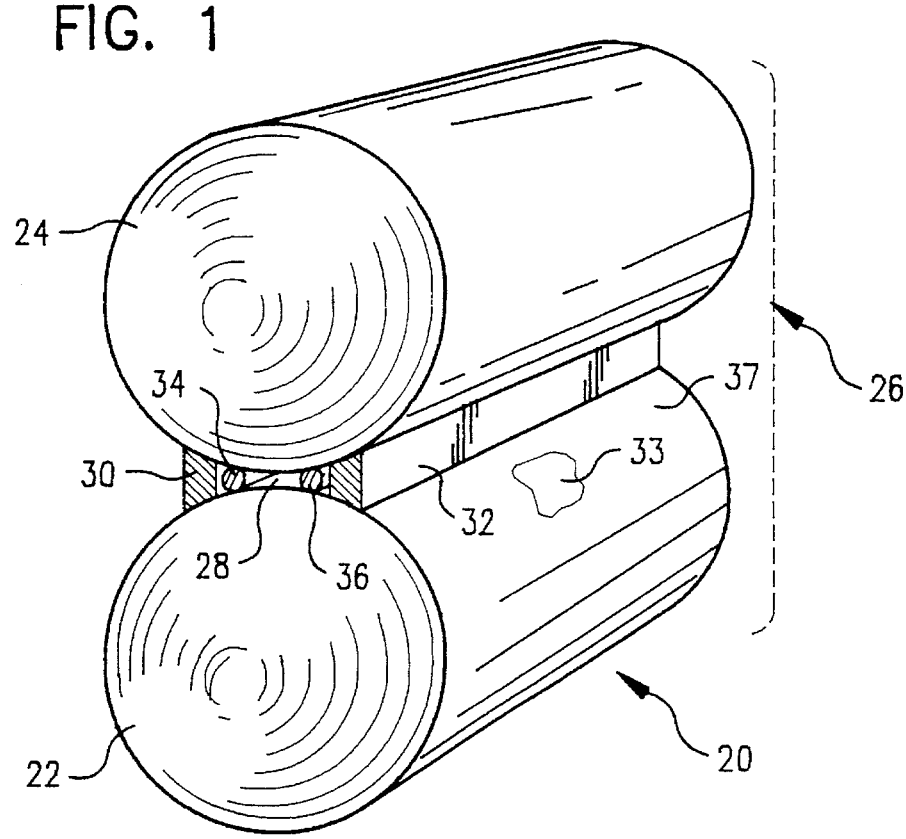
FIG. 1 is a fragmentary view of a structure fabricated from logs which are protected against insecticidal and fungal infestation with a slow release preservative in accord with the principles of the present invention.

The novel wood preservatives of the present invention are paste-type compositions which employ a pesticidally active boron compound or a mixture of such compounds as the active ingredient. The pesticide is dispersed in a mixture of polyethylene glycols (PEG's) so selected as to: (1) give the composition the wanted toothpastelike consistency; (2) make the active ingredient available over an extended period of time; and (3) promote the penetration of the active principle into the wood being protected, especially during periods when damage to the wood is most apt to occur absent the protection afforded by the preservative. A surfactant component is preferably employed to promote the dispersion of the boron component in the PEG's and to reduce the surface tension of the pesticide formulation as it is applied to the wood to be protected. This enhances surface wetting of the substrate to which the formulations is applied. Surface wetting is important because it causes the preservative to stick to the substrate being treated instead of rolling to an unwanted, less effective location or even off the substrate.

The preferred active ingredient is disodium octoborate tetrahydrate (DOT). That material is available in a 98 percent concentration with 2 percent absorbed moisture and the formula $Na_2B_8O_{13}.4H_2O$ from the U.S. Borax Corporation under the tradename TIMBOR®. DOT is a soluble white powder which provides long lasting protection to wood. It is free of unpleasant odors, does not change the appearance of wood, and is easy to handle. DOT is not corrosive to most metals, has very low acute toxicity, is not absorbed through the skin, is easily removed by soap and water, and is highly toxic to woodinfecting insects and fungi.

Although DOT is preferred, there are other, pesticidally active boron compounds that can be employed in the practice of the present invention. These include: boric acid; borax/boric acid mixtures; potassium, ammonium, and sodium borates; anhydrous borax; borax pentahydrate; and boric oxide.

The preferred carrier-thickener is a mixture of two PEG's, one a liquid with a molecular weight preferably in the range of 190 to 210 and the second a solid with a molecular weight preferably in the range of 4400 to 4800 but in any event high enough that the preservative will not melt if left in or otherwise exposed to the sun. Commercial products that meet these specifications are CARBOWAX 200 which is a liquid PEG with an approximate molecular weight of 200 and CARBOWAX 4600 flake, a solid PEG with an approximate molecular weight of 4600. Both PEG's are available from the Union Carbide Chemicals & Plastics Technology Corporation.

The mixture of PEG's is required to obtain the wanted toothpastelike consistency at the temperatures at which the formulation is applied and activated. Both the higher molecular weight PEG and the lower molecular weight PEG are resistant to evaporation. They accordingly keep the active principle available for release and transport into the wood being protected by the same moisture which creates the conditions favorable for pesticidal invasion. Both PEG's are also water-miscible, which advantageously enhances the moisture-triggered penetration of the active ingredient into the wood being protected by the preservative.

The preferred DOT pesticide is not soluble enough in water for that carrier by itself to be loaded to the extent required for pesticidal effectiveness. The problem this creates is eliminated and solubility promoted by the liquid PEG. That constituent predisperses the DOT and thereby facilitates its solution in the moisture which contacts the emplaced wood preservative. The PEG is hygroscopic and a diluent, these mechanisms acting in concert to effect and enhance penetration of the wood by the selected boron pesticide better than water alone can.

Either one surfactant or a combination of two surfactants can be employed in the formulation. If two surfactants are used, one is employed to promote the dispersion of the active ingredient in the PEG carrier and to keep that ingredient uniformly suspended in the carrier. The second surfactant is a wetting agent utilized to reduce the surface tension of the preservative formulation. As discussed above, this is important because of the adhesion to the substrate to keep the formulation in place that is consequentially obtained. One suitable dispersant is VANWET 9N9, which is a non-ionic, ethoxylated phenol supplied by Univar Corporation, Seattle, Wash.; and this can surfactant be used alone, functioning both as a wetting agent and a dispersant. A wetting agent that can be used in combination with VANWET 9N9 is FLUORAD FC-129, a surfactant manufactured by the Minnesota Mining and Manufacturing company.

The novel wood preservatives of the present invention are formulated as follows.

| Constituent | Weight Percent (Range) |
| --- | --- |
| Boron-based Pesticide (active ingredient) | 37–55.5 |
| Solid PEG | 1–10 |
| Liquid PEG | 40–60 |
| Dispersant | 0.01–5 |
| Wetting/Adhesion Agent | 1–10 |

In the foregoing table, the percentages are approximate (i.e., nominal); and the weight percent of the boron-based pesticide is expressed as the boric acid equivalent (BAE). The amount of a particular pesticide can be calculated in straightforward fashion from the BAE. The conversion factor is 1.2 for TIMBOR® as one example (i.e., DOT (TIMBOR®) equals BAE divided by 1.2).

With perhaps some sacrifice in long-term effectiveness and/or ease of application, the dispersant and/or the adhesion agent can be omitted from the formulation if warranted by a particular application of the invention.

A representative, preferred wood preservative embodying the principles of the present invention was formulated as follows:

| Constituent | Weight (lbs) | Weight Percent |
| --- | --- | --- |
| PEG 200 | 155.50 | 50.15 |
| PEG 4600 (Flake) | 10.00 | 3.22 |
| TIMBOR | 119.60 | 38.57 |
| Vanwet 9N9 (Dispersant) | 1.00 | 0.32 |
| Propylene Glycol (Wetting/Adhesion Agent) | 24.00 | 7.74 |

A suitable batch-type method of preparing this representative preservative utilizes a 20 horsepower, single-shaft Hi-Speed Disperser with: a vertical shaft; a Cowles type blade depending into a 300 gallon, dished-bottom, cylindrical tank; and a ball-valve type discharge port on the side of the tank near its bottom. The constituents of the pesticidal formulation are charged into the tank from a position above its open upper end.

The specific procedure is as follows:

(1) Measure the propylene glycol and the PEG 200 (the low molecular weight polyethylene glycol), and add these to the tank. The order of addition is not critical;

(2) turn on the mixer at the lowest speed which will create a vortex in the liquids;

(3) activate the heating mechanism (the glycols heat slowly, making heating at this point important);

(4) add the heated glycols to the tank;

(5) add the surfactant to the tank and mix with the glycols;

(6) measure the DOT and add it gradually to the tank with agitation;

(7) continue to agitate and heat the mixture until the DOT is well mixed;

(8) measure the PEG 4600, and add it to the tank with continued heat and agitation; and (9) maintain the temperature at 180° F. and continue to agitate at a speed which gives a vortex 5–10 inches above the blade until the mixture is smooth and uniform.

Referring now to the drawing, FIG. 1 depicts, in fragmentary form, a log structure 20 such as a house or outbuilding fabricated in part by erecting circularly sectioned logs such as those identified by reference characters 22 and 24 in a vertical array to form a wall 26. The gap 28 between logs 22 and 24 is sealed, typically with a synthetic chinking such as that sold by Perma-Chink Systems, Inc., Redmond, Wash. under the trademark PERMACHINK® (the chinking is identified in FIG. 1 by reference characters 30 and 32). The logs are then typically stained, using a brush or spray applicator and a latex or other polymerizable stain 33 or an oil stain.

In accord with the present invention, structure 20 is protected against insecticidal and fungal damage by two parallel beads 34 and 36 of wood preservative of the formulation and with the paste-like consistency described above. By virtue of it having a consistency of this character, the beads 34 and 36 of preservative may be applied with a conventional caulking gun although other applicators can instead be employed, if desired. Preservative beads 34 and 36 are applied to the top of the external surface 37 of log 22 prior to the stacking of log 24 on log 22 in a parallel, spaced (or side-by-side) relationship. The beads extend the length of the log.

When moisture penetrates the logs 22 and 24 in the location of the preservative composition, the pesticidally active boron compound will be released from the beads 34 and 36 of wood preservative and transported into logs 22 and 24 to protect them against insecticidal and fungal attack. As discussed above, this relied upon penetration of the boron-based pesticide is significantly facilitated by the water-miscible, higher molecular weight PEG and by the penetrating action of the lower molecular weight PEG.

When the moisture content increases in timbers 22 and 24, the timbers are more susceptible to damage by fungi and insects. However, a higher level of moisture in the timbers increases the rate at which the active ingredient diffuses from the beads 34 and 36 into the wood to resist the intrusion of the fungi or insects. Thus, the conditions which made the timbers more susceptible to pesticidal attack also release and transport the active boron in a manner which results in optimal kill of any deleterious insects and/or fungi that might be present.

When the wood is rather dry, it is substantially less susceptible to damage by fungi and insects; and the diffusion rate of the active ingredient into the wood structure is substantially lower. As a consequence, the preservative beads remain effective over an extended period of many years because the active ingredient diffuses into the wood essentially only when and to the extent that it is needed.

It is important, in applying the preservative, that the amount of the preservative be matched to the size or volume of the wooden member being treated. Application rates which will provide a boron pesticide concentration in the range of 0.05 to 0.24 pounds per cubic foot of substrate at a depth of 0.75 in are employed. The optimal concentrations depend to some extent upon the aggressiveness and/or species of the insect(s) or fungus(ii) to be controlled and can be obtained by applying beads with equivalent diameters related to the substrate diameter as follows:

TABLE 1

| Substrate Diameter (in) | Preferred Equivalent Diameter of Preservative Bead (in) |
| --- | --- |
| 6 | 0.18* |
| 8 | 0.21* |
| 10 | 0.22* |
| 12 | 0.25* |

*–0 + 20 percent

With regard to the term of "equivalent diameter", the pastelike composition will normally be dispensed in a bead which is about three-sixteenths of an inch in diameter and possibly up to three-eighths of an inch in diameter. Equivalent diameter is the diameter of a circular cross-section of the pastelike composition equalling the total cross-sectional of the bead or beads that are applied. For example, if the bead of the composition being dispensed has a diameter of one-quarter inch, and if the wanted "equivalent diameter" is one-half inch, four one-quarter inch diameter bead would be applied to the timber to provide the "equivalent diameter" of one-half inch.

It is typically difficult to apply beads of a diameter which exceed about one-quarter to three-eighths of an inch. In many instances, therefore, it is common to apply two or more beads to obtain the required total volume.

For components that do not have a circular cross-section, the equivalent diameter is calculated as if the component were a round timber with a cross-section of the same area. Thus, for purposes of calculating equivalent bead diameter, a 6 in×12 in beam is treated as if it were a round log with a diameter ≈10 in.

If the nature of the wood, the weather conditions, the types of insects and fungi that may be attacking the wood, and other factors are such that more of the composition is required, the equivalent diameters given in Table 1 can be increased by as much as 25 to 200 percent, an upper limit beyond which there is typically no particular benefit in applying more of the composition. Also, the equivalent diameter as given in the above table can possibly be decreased by 10 to 50 percent if the relevant conditions are less severe.

Figure 2:
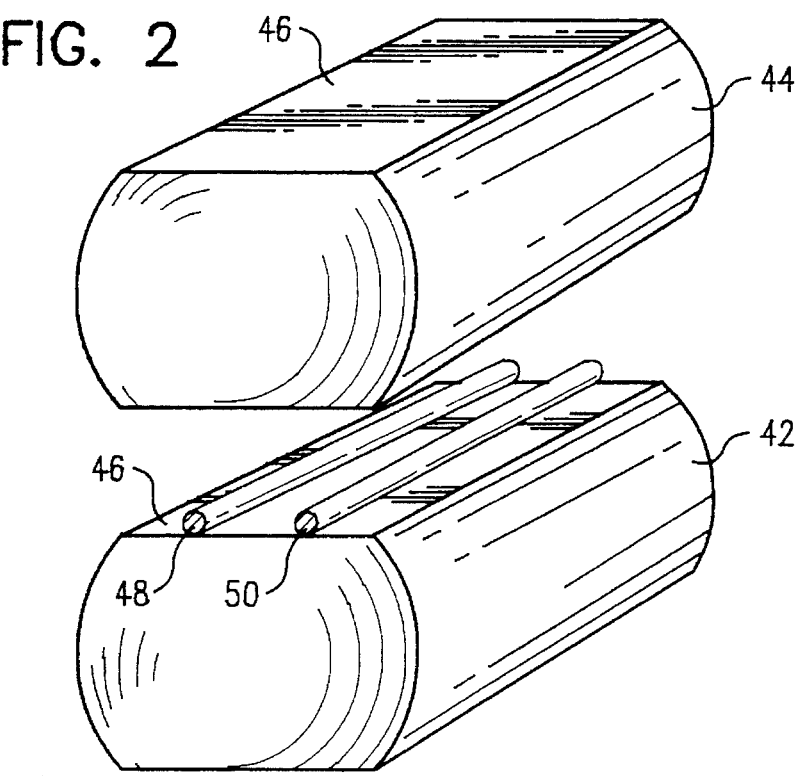
FIG. 2 is an exploded, fragmentary view of a structure fabricated of squared off logs, showing how the preservative is applied.

Logs, timbers, and other structural products are used in a wide variety of forms including the round logs 22 and 24 shown in FIG. 1 and squared-off logs such as those illustrated in FIG. 2 and identified by reference characters 42 and 44. These logs have flat upper surfaces 46 and parallel, also flat lower surfaces (not shown). In building a structure from logs of the character shown in FIG. 2, one or more beads of preservative—in this case two beads 48 and 50—are applied to the upper surface 46 of lower log 42 before the next log 44 is stacked on it.

Often employed in wooden structures are rectangularly sectioned logs such as those depicted in FIG. 3 and identified by reference characters 54 and 56. Also common is the assembly technique illustrated in FIG. 3 in which beams of the illustrated character are separated by vertically oriented, parallel, spaced apart splines 58 and 60. The upper and lower edges of these splines are respectively seated in grooves 62 in the lower surface 64 of upper beam 56 and in complementary grooves 66 formed in the upper surface 68 of lower beam 54.

In erecting a structure of the character depicted in FIG. 3, the beads of preservative—here those identified by reference characters 70 and 72—are applied to the upper surface 68 of beam 54 before splines 58 and 60 are installed and the upper beam 56 lowered into place.

As is also shown in FIG. 3, it is not essential that the wood preservatives of the present invention be applied to exterior surfaces of the wood being treated. An alternative is to drill or otherwise provide a hole or other cavity such as that identified by reference character 74 in the wooden structural member and then place the preservative in that hole. This can also be done in most any other log configuration.

As shown in FIG. 3, holes of the character just described will typically, if not necessarily, be spaced at intervals along the wooden component being treated. The spacing, diameter, and depth of the holes and the amount of wood preservative placed in them are so coordinated that the amount of the preservative will be within the concentration/depth parameters identified above.

Another representative, and typical, application of the present invention is illustrated in FIG. 4. That figure depicts, in fragmentary form, a log structure 78 with a vertical wall 80. Wall 80 has a rectangular opening 82 in which a window 84 is installed. The window is held in place by a frame 86 composed of upper, lower, and vertical members 88, 90, 92, and 94. This window frame has an inwardly facing groove 96 in which the edges 98 of the window are seated (see FIG. 6). The gaps between the window frames and the ends 100 of the logs 102 making up wall 80 are filled with chinking 104 as are the gaps 106 between adjacent logs.

In structure 78, logs 102 are protected from insecticidal and fungal attack with a wood preservative of the character discussed above and applied to the horizontal surfaces of the logs or placed in holes drilled in them. Also, in structure 78, wooden window frame 86 is protected against insecticidal and fungal attack with the wood preservative.

All four components 88 . . . 94 of the frame are treated in the same manner. Vertical frame member 94 is typical. As shown in FIG. 5, a bead 108 of the preservative is placed on the exterior surface 110 of that component midway between its inner and outer edges 112 and 114 before the gap between component 94 and the end 100 of log 102 is filled with chinking 104. Wood preservative bead 108 extends the length of window frame component 94 and has a diameter large enough to provide at least the minimum active ingredient at depth concentration identified above.

In applications of the invention such as those just described with reference to the drawing, the chinking 30 and 32 (FIG. 1) and 104 (FIGS. 4 and 5) and the splines 58 and 60 (FIG. 3) perform several important preservative-related functions. They protect the wood preservative from the elements, keeping it from being dissolved or otherwise broken down and washed away or rendered ineffective in other ways by direct exposure to the elements; e.g., to a driving rain. The chinking and splines also hide the beads of preservative, which some may find aesthetically unattractive.

Also, the chinking and splines isolate the beads of wood preservative from those areas which are commonly stained to enhance the appearance of the structure; e.g., those exterior log surfaces identified by reference character 33 in FIG. 1. This prevents preservative constituents (i.e., the carrier) from interfering with the curing mechanism intended to take place as the stain dries.

FIG. 6 shows another type of log or timber in which the present invention can be advantageously used. The log 120 has upper and lower flattened surfaces 122 and 124. The upper portion of the log has a central, relatively deep, vertical kerf 126 which extends nearly to the centerline of the log 120. It also has two, laterally spaced, more shallow kerfs 128 and 130 which fit into ridges or elongated protrusions 132 and 134 of a similarly formed log (not shown) immediately above log 120. The composition is applied in kerf 126. As this kerf cuts across the grain of the wood, the active boron ingredient is better able to travel along diffusion paths parallel to the grain and thus more easily reach the various interior portions of log 120.

FIG. 7 shows a round log 136 having a single, radially extending kerf 138. The bead or beads of the preservative composition are inserted in this kerf, thus obtaining the advantage of diffusion along paths parallel to the grain of the wood to the more critical areas of the log.

It will be readily apparent to those skilled in the relevant arts that an essentially endless variety of wooden components may be protected from insecticidal and fungal attack by employing the wood preservative formulations and application techniques of the present invention. To the extent that these are not expressly excluded from the appended claims, they are fully intended to be embraced by those claims.

It will also be appreciated that this novel technique of applying a paste preservative with a moisture activated translocation of the active principle to the interior of a wooden member or component to protect it against insecticidal and fungal attack is not confined to the use of a boron-based material as the active principle or even to the use of the specific carrier constituents identified above as long as constituents with the requisite characteristics are selected. Consequently, such modifications of the invention are also fully intended to be covered by the appended claims.

Essentially the only limitation on the use of the preservative is that it must be protected from conditions such as driving rains which might break down and wash the preservative from the wood surface. Also, as discussed above, the preservative should be isolated from any exposed areas to which a latex or other film-forming polymer is to be applied so that the active principle of the preservative will not interfere with the curing mechanism. In addition, for purely aesthetic reasons, it may be preferable to hide the preservative from view.

The invention may thus be embodied in many forms without departing from the spirit or essential characteristics of the invention. The present embodiments are therefore to be considered in all respects as illustrative and not restrictive, the scope of the invention being indicated by the appended claims rather than by the foregoing description. All changes which come within the meaning and range of equivalency of the claims are therefore intended to be embraced therein.

What is claimed is:

1. A controlled release wood preservative which is effective against insects and fungi and which comprises a boron-based pesticide dispersed in a carrier, said carrier comprising both a solid polyethylene glycol and a liquid polyethylene glycol and said pesticide being present in an amount such that said preservative is effective to protect wood against insecticidal and fungal attack.

2. A controlled release wood preservative as defined in claim 1 in which the pesticide comprises borax; boric acid; a mixture of borax and boric acid; borax pentahydrate; a potassium, ammonium, or sodium borate; disodium octoborate; or disodium octoborate tetrahydrate.

3. A controlled release wood preservative as defined in claim 2 in which the pesticide is disodium octoborate or disodium octoborate tetrahydrate.

4. A controlled release wood preservative as defined in claim 1 which contains from about 37 to 55.5 weight percent of the pesticide calculated as the boric acid equivalent.

5. A controlled release wood preservative as defined in claim 1 in which at least one of the polyethylene glycols is water-miscible and is effective, when the preservative is contacted by moisture, to enhance a translocation of the pesticide into and throughout wood to which the preservative is applied.

6. A controlled release wood preservative as defined in claim 1 which comprises a surfactant constituent which is effective to uniformly disperse the pesticide in the carrier.

7. A controlled release wood preservative as defined in claim 1 which comprises:

| Constituent | Weight Percent |
| --- | --- |
| Boron-based Pesticide (calculated as the boric acid equivalent) | 37–55.5 |
| Liquid Polyethylene Glycol | 40–60 |
| Solid Polyethylene Glycol | 1–10. |

8. A wood preservative as defined claim 7 which comprises from about 0.01 to 5 weight percent of a surfactant constituent which is effective to promote uniform suspension of said pesticide in the carrier of the wood preservative.

9. A wood preservative as defined in claim 7 which comprises from about 1 to 10 weight percent of a surfactant constituent which is effective to promote adhesion of said preservative to a surface to which the preservative is applied.

* * * * *